US006828145B2

(12) United States Patent
Avital et al.

(10) Patent No.: US 6,828,145 B2
(45) Date of Patent: Dec. 7, 2004

(54) METHOD FOR THE ISOLATION OF STEM CELLS BY IMMUNO-LABELING WITH HLA/MHC GENE PRODUCT MARKER

(75) Inventors: Itzhak Avital, Los Angeles, CA (US); Walid Arnaout, Calabasas, CA (US); Daniel Inderbitzin, Zurich (CH)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/852,458

(22) Filed: May 9, 2001

(65) Prior Publication Data

US 2002/0119564 A1 Aug. 29, 2002

Related U.S. Application Data

(60) Provisional application No. 60/202,979, filed on May 10, 2000.

(51) Int. Cl.[7] .............................. C12N 5/00; C12N 5/06; G01N 33/53
(52) U.S. Cl. .......................... 435/325; 435/326; 435/7.1
(58) Field of Search ................................. 435/325, 326, 435/7.1, 383, 4, 7.21, 173.4, 377, 343, 343.2

(56) References Cited

U.S. PATENT DOCUMENTS

| | | | |
|---|---|---|---|
| 4,714,680 A | 12/1987 | Civin | 435/240.25 |
| 4,965,204 A | 10/1990 | Civin | 435/240.27 |
| 5,035,994 A | 7/1991 | Civin | 435/2 |
| 5,130,144 A | 7/1992 | Civin | 424/577 |
| 5,166,065 A | 11/1992 | Williams et al. | 435/240.1 |
| 5,429,938 A | 7/1995 | Humes | 435/240.2 |
| 5,436,151 A | 7/1995 | McGlave et al. | 435/240.1 |
| 5,437,994 A | 8/1995 | Emerson et al. | 435/240.2 |
| 5,449,620 A | 9/1995 | Khillan | 435/284 |
| 5,556,783 A | 9/1996 | Lavker et al. | 435/240.21 |
| 5,589,376 A | 12/1996 | Anderson et al. | 435/240.4 |
| 5,643,741 A | 7/1997 | Tsukamoto et al. | 435/7.24 |
| 5,646,043 A | 7/1997 | Emerson et al. | 435/373 |
| 5,654,183 A | 8/1997 | Anderson et al. | 435/172.3 |
| 5,665,557 A | 9/1997 | Murray et al. | 435/7.24 |
| 5,670,351 A | 9/1997 | Emerson et al. | 435/172.3 |
| 5,672,499 A | 9/1997 | Anderson et al. | 435/240.4 |
| 5,677,136 A | 10/1997 | Simmons et al. | 435/7.24 |
| 5,681,559 A | 10/1997 | DiGiusto et al. | 424/93.1 |
| 5,693,482 A | 12/1997 | Anderson et al. | 435/29 |
| 5,728,581 A | 3/1998 | Schwartz et al. | 435/385 |
| 5,753,506 A | 5/1998 | Johe | 435/377 |
| 5,772,994 A | 6/1998 | Ildstad et al. | 424/93.7 |
| 5,806,529 A | 9/1998 | Reisner et al. | 128/898 |
| 5,824,489 A | 10/1998 | Anderson et al. | 435/7.21 |
| 5,843,780 A | 12/1998 | Thomson | 435/363 |
| 5,849,553 A | 12/1998 | Anderson et al. | 435/172.3 |
| 5,912,133 A | 6/1999 | Lemischka | 435/7.21 |
| 5,928,947 A | 7/1999 | Anderson et al. | 435/455 |
| 5,965,436 A | 10/1999 | Thiede et al. | 435/372 |
| 5,968,829 A | 10/1999 | Carpenter | 435/467 |
| 6,040,180 A | 3/2000 | Johe | 435/377 |
| 6,090,622 A | 7/2000 | Gearhart et al. | 435/366 |
| 6,140,116 A | 10/2000 | Dinsmore | 435/325 |
| 6,200,806 B1 | 3/2001 | Thomson | 435/366 |
| 6,204,053 B1 | 3/2001 | Dinsmore | 435/325 |

FOREIGN PATENT DOCUMENTS

| | | |
|---|---|---|
| EP | 0695351 | 8/1999 |
| JP | 11017624 | 1/1999 |

OTHER PUBLICATIONS

Thomson, J.A. et al. Embryonic Stem Cell Lines Derived from Human Blastocysts. Science 1998, 282:1145–1147.*
Roit, I. et al. Immunology. C.V. Mosby Company, Ltd. 1987, pp. 4.10–4.11.*
D. Van Der Kooy et al., "Why Stem Cells?" *Science*, vol. 287, pp. 1439–1441 (Feb. 25, 2000).
V. Rukshin et al., "Intravenous Magnesium in Experimental Stent Thrombosis in Swine," *Arteriosclerosis, Thrombosis and Vascular Biology*, vol. 21, No. 9, pp. 1544–1549 (Sep. 1, 2001).
S. D. Gertz et al., "Effect of Magnesium Sulfate on Thrombus Formation Following Partial Arterial Constriction: Implications for Coronary Vasospasm," *Magnesium*, vol. 6, No. 5, pp. 225–235 (1987).
H–D Claus, "Zur Frage der Wirksamkeit einer Thromboembolieprophylaxe durch Magnesium bei der Kontakttherapie von Portio– und Korpuskarzinomen der Uterus mit Gammastrahlern," *Strahlentherapie*, vol. 135, No. 3, pp. 291–294 (Mar. 1968).
H.B. Ravn et al., "Magnesium Inhibits Platelet Activity–an Infusion Study in Healthy Volunteers," *Thrombosis and Haemostasis*, vol. 75, No. 6, pp. 939–944 (Jun. 1996).
J.A. Thomson et al., "Embryonic Stem Cell Lines Derived from Human Blastocysts," *Science*, vol. 282, pp. 1145–1147 (Nov. 6, 1998).
D. W. Pincus et al., "Fibroblast Growth Factor—2/Brain–Derived Neurotrophic Factor–Associated Maturation of New Neurons Generated from Adult Human Subependymal Cells," *Annals of Neurology*, vol. 43, No. 5, pp. 576–585 (May 1998).

(List continued on next page.)

*Primary Examiner*—Deborah Crouch
*Assistant Examiner*—Thaian N. Ton
(74) *Attorney, Agent, or Firm*—Pillsbury Winthrop LLP (57) ABSTRACT

Disclosed herein is the discovery that mammalian stem cells do not express $\beta_2$microglobulin ($\beta_2$m). The invention discloses a method of isolating stem cells comprising sorting, from a sample of cells, cells that express $\beta_2$m from cells that do not express $\beta_2$m. One then selects stem cells from the population of cells that does not express $\beta_2$m. This is accomplished by selecting cells that express a known marker, such as proteins expressed by genes encoding the major histocompatibility complex. An isolated stem cell is disclosed, as is a method for identifying it and other stem cells.

34 Claims, 4 Drawing Sheets

(3 of 4 Drawing Sheet(s) Filed in Color)

OTHER PUBLICATIONS

C. B. Johansson et al., "Rapid Communication—Neural Stem Cells in the Adult Human Brain," *Experimental Cell Research*, vol. 253, pp. 733–736 (1999).

S. F. Pagano et al., "Isolation and Characterization of Neural Stem Cells from the Adult Human Olfactory Bulb," *Stem Cells 2000*, vol. 18, pp. 295–300 (2000).

U. Lendahl et al., "CNS Stem Cells Express a New Class of Intermediate Filament Protein," *Cell*, vol. 60, No. 4, pp. 585–595 (Feb. 1990).

J. G. Toma et al., "Isolation of multipotent adult stem cells from the dermis of mammalian skin," *Nature Cell Biology*, vol. 3, pp. 778–784 (2001).

E. Mezey et al., "Turning Blood into Brain: Cells Bearing Neuronal Antigens Generated in Vivo from Bone Marrow," *Science*, vol. 290, pp. 1779–1782 (Dec. 2000).

T. R. Brazelton et al., "From Marrow to Brain: Expression of Neuronal Phenotypes in Adult Mice," *Science*, vol. 290, pp. 1775–1779 (Dec. 2000).

M. A. Eglitis and E. Mezey, "Hematopoietic cells differentiate into both microglia and macroglia in the brains of adult mice," *Proc. National Academy of Science USA/Neurobiology*, vol. 94, pp. 4080–4085 (Apr. 1997).

D. Woodbury et al., "Adult Rat and Human Bone Marrow Stromal Cells Differentiate Into Neurons," *Journal of Neuroscience Research*, vol. 61, pp. 364–370 (2000).

J. Sanchez–Ramos et al., "Adult Bone Marrow Stromal Cells Differentiate into Neural Cells in Vitro,"*Experimental Neurology*, vol. 164, pp. 247–256 (2000).

Vogel, Gretchen; "Can Old Cells Learn New Tricks," *The American Association for the Advancement of Science*, vol. 287, No. 5457, pp. 1418–1419 (Feb. 25, 2000).

Vogel, Gretchen; "Capturing the Promise of Youth," *The American Association for the Advancement of Science*, vol. 286, No. 5448, pp. 2238–2239 (Dec. 17, 1999).

Weismann, Irving L.; "Translating Stem and Progenitor Cell Biology to the Clinic: Barriers and Opportunities," *The American Association for the Advancement of Science*, vol. 287, No. 5457, pp. 1442–1446 (Feb. 25, 2000).

Barinaga, Marcia; "Fetal Neuron Grafts Pave the Way for Stem Cell Therapies," *The American Association for the Advancement of Science*, vol. 287, No. 5457, pp. 1421–1422 (Feb. 25, 2000).

* cited by examiner

METHOD FOR THE ISOLATION OF STEM CELLS BY IMMUNO-LABELING WITH HLA/MHC GENE PRODUCT MARKER

This application claims the benefit of priority under 35 U.S.C. § 119(e) of provisional application serial No. 60/202,979, filed May 10, 2000, the contents of which are hereby incorporated by reference.

FIELD OF THE INVENTION

Embodiments of the present invention are directed to a method for isolating mammalian stem cells from a population of cells by immunolabeling the population of cells with MHC/HLA gene-product markers. Further embodiments of the present invention are directed to the purification and enrichment of cells so isolated.

BACKGROUND OF THE INVENTION

Nearly every cell in an animal's body, from neural to blood to bone, owes its existence to a stem cell. A stem cell is commonly defined as a cell that (i) is capable of renewing itself; and (ii) can give rise to more than one type of cell (that is, a differentiated cell) through asymmetric cell division. F. M. Watt and B. L. M. Hogan, "Out of Eden: Stem Cells and Their Niches," Science, 284, 1427–1430 (2000). Stem cells give rise to a type of stem cell called progenitor cells; progenitor cells, in turn, proliferate into the differentiated cells that populate the body.

The prior art describes the development, from stem cell to differentiated cells, of various tissues throughout the body. U.S. Pat. No. 5,811,301, for example, the disclosure of which is hereby incorporated by reference, describes the process of hematopoiesis, the development of the various cells that comprise blood. The process begins with what may be a pluripotent stem cell, a cell that can give rise to every cell of an organism (there is only one cell that exhibits greater developmental plasticity than a pluripotent stem cell; this is a fertilized ovum, a single, totipotent stem cell that can give rise to an entire organism when implanted into the uterus). The pluripotent stem cell gives rise to a myeloid stem cell. Certain maturation-promoting polypeptides cause the myeloid stem cell to differentiate into precursor cells, which in turn differentiate into various progenitor cells. It is the progenitor cells that proliferate into the various lymphocytes, neutrophils, macrophages, and other cells that comprise blood tissue of the body.

This description of hematopoiesis is vastly incomplete, of course: biology has yet to determine a complete lineage for all the cells of the blood (e.g., it is has yet to identify all the precursor cells between the myeloid stem cell and the progenitor cells to which it gives rise), and it has yet to determine precisely how or why the myeloid cell differentiates into progenitor cells. Even so, hematopoiesis is particularly well studied; even less is known of the development of other organ systems. With respect to the brain and its development, for example, U.S. Pat. No. 6,040,180, the disclosure of which is hereby incorporated by reference, describes the "current lack of understanding of histogenesis during brain development." U.S. Pat. No. 5,849,553, the disclosure of which is hereby also incorporated by reference, describes the "uncertainty in the art concerning the development potential of neural crest cells."

The identification and isolation of stem cells has daunted researchers for decades. To date, no one has identified an individual neural stem cell or hematopoietic stem cell. F. H. Gage, "Mammalian Neural Stem Cells," Science, 287, 1433–1488 (2000). There are two principal difficulties. First, stem cells are rare. In bone marrow, for example, where hematopoiesis occurs, there is only one stem cell for every several billion bone marrow cells. G. Vogel, "Can Old Cells Learn New Tricks?" Science, 287, 1418–1419 (2000). Second, and more importantly, researchers have heretofore been unable to identify molecular markers which are unique to stem cells; to the typical immunoassay, most stem cells look like any other cell. Id. Compounding this problem is that primitive stem cells may be in a quiescent state. As a result, they may express few molecular markers. F. H. Gage, supra.

A method to identify and effectively isolate stem cells would be of immense importance. Researchers are already transplanting immature neurons, presumed to contain neural stem cells, from human fetuses to adult patients with neurodegenerative disease. The procedure has reduced symptoms by up to 50% in patients with Parkinson's disease in one study. M. Barinaga, "Fetal Neuron Grafts Pave the Way for Stem Cell Therapies," Science, 287, 1421–1422 (2000). Many of the shortcomings of this procedure, including the ethical and practical difficulties of using material derived from fetuses, could be addressed by using cultures of isolated stem cells, or stem cells obtained from adult individuals.

Transplantation of purified hematopoietic stem cells could replace bone marrow transplants. Such stem cells are free of contamination with cancer cells, and could induce life-long tolerance of donor organ or tissue transplants. I. L. Weissman, "Translating Stem and Progenitor Cell Biology to the Clinic: Barriers and Opportunities," Science, 287, 1442–1446 (2000). Transplantation of islet stem cells could replace insulin therapy; skeletal muscle stem cell transplants could treat patients with life-threatening muscle loss, such as can occur with muscular dystrophy; and transplantation of heart muscle stem cells could be used to regenerate heart muscle ravaged by myocardial infarction. Id. There are many more important uses, but one must first have the starting material—the stem cells that make these uses possible—before they may be investigated and applied. The invention described herein is the first to provide that starting material.

BRIEF DESCRIPTION OF THE FIGURES

The file of this patent contains at least one drawing executed in color. Copies of this patent with color drawing(s) will be provided by the patent and Trademark Office upon request and payment of the necessary fee.

FIG. 1A shows cells stained for $\beta_2$m in a whole-cell isolation from 24-days-old rats. The blue discoloration represents cells that do not express $\beta_2$m ($\beta_2$m$^-$).

FIG. 1B shows $\beta_2$m$^-$ cells cyto-spun after whole cell isolation from rats subjected to common bile duct ligation on day 10.

FIG. 1C shows $\beta_2m^-$ cells after whole-cell isolation from rats subjected to common bile duct ligation on day 21. These cells have an oval shape, unlike the small dense, cells shown in FIG. 1A.

FIG. 1D shows $\beta_2m^-$ cells from paraffin sections of human liver (PSC).

FIG. 1E shows positive Thy-1 staining of $\beta_2m^-$ cells after whole-cell isolation from rats subjected to common bile duct ligation on day 21. These cells also have an oval shape, unlike the small, dense cells shown in FIG. 1A (the stain used on the cells shown in FIG. E is the same as that used on the cells shown in FIG. 1C).

FIG. 1F shows $\beta_2m^-$ cells "streaming" from portal tracts in liver cells prepared after 21 days from rats that underwent common bile ligation.

FIG. 2A shows bone marrow-derived hepatocyte stem cells stained positive for ALB.

FIG. 2B shows bone marrow-derived hepatocyte stem cells stained positive for AFP.

FIG. 2C shows bone marrow-derived hepatocyte stem cells stained positive for CK8.

FIG. 2D shows bone marrow-derived hepatocyte stem cells stained positive for CIEBPα.

FIG. 2E shows the results of RT-PCR on bone marrow-derived hepatocyte stem cells purified from bone marrow on day 10. The bone marrow was obtained from rats that had underwent common bile duct ligation. Expression of ALB, CIEBPα, HNF-4 but not IINF-1 is seen. "MW STD" refers to molecular weight standard; β-actin was used as positive systematic control and normal hepatocytes were used as gene specific positive control.

FIG. 2F shows bone marrow-derived hepatocyte stem cells stained positive for ALB.

FIG. 2G shows the results of RT-PCR on bone marrow-derived hepatocyte stem cells purified from human normal bone marrow. Expression of ALB and CIEBP is seen. Negative control with rat albumin primers was used.

FIG. 4A is a three-dimensional digital reconstruction, utilizing confocal microscopy, of bone marrow-derived hepatocyte stem cells (cells were micro-dissected from culture and plated on slides for immunofluorescence studies). Red indicates CAM5.2 and green indicates albumin.

FIG. 4B shows immunofluorescence of bone marrow-derived hepatocyte stem cells in culture; green indicates albumin.

FIG. 4C shows the results of RT-PCR on bone marrow-derived hepatocyte stem cells in culture, expressing albumin, HNF-1 and CEBP/α.

FIG. 4D shows fresh bone marrow-derived hepatocyte stem cells 1hr in culture.

FIG. 4E shows bone marrow-derived hepatocyte stem cells after 7 days in culture.

FIG. 4F shows the results of electron microscopy, demonstrating the hepatocytic ultra structure of bone marrow-derived hepatocyte stem cells in culture. The full arrow is pointing at villi; the empty arrow is pointing at glycogen granules.

DETAILED DESCRIPTION OF THE INVENTION

The inventors have discovered that many stem cells, including, for example, liver, spleen, and neuronal stem cells, do not express $\beta_2$microglobulin ("$\beta_2m$"). This is a surprise, because $\beta_2m$ is among the least polymorphic and the most-conserved immune molecules in nature. It appears on all cells that have a nucleus—that is, on the cells of every bird, mammal, and all other animals. Only a few cells are known to lack it, such as spermatazoa and certain cells at the inner cell membrane of an embryo. When $\beta_2m$ appears with class I molecules of the major histocompatibility complex ("MHC") it functions to stabilize the alpha chain of these molecules and facilitate antigen transport. No other role is known for it. Most $\beta_2m$ is expressed on the cell surface without class-I molecules, however. There, its function is unknown.

The method of the invention identifies stem cells by obtaining a sample of cells, and then sorting from the sample cells that express $\beta_2m$ from cells that do not. The sample that expresses $\beta_2m$ is referred to as $\beta_2$microglobulin positive ($\beta_2m^+$); the sample that does not express $\beta_2m$ is referred to as $\beta_2$microglobulin negative ($\beta_2m^-$). It is the $\beta_2m^-$ sample that contains stems cells.

The inventors have discovered that $\beta_2m^-$ cells are among the earliest of stem cells and may be the "ultimate" stem cells—true isolated embryonal stem cells that researchers have sought for years without success to isolate. Such cells can remain dormant throughout development until activated in a mature adult organism.

One identifies stem cells according to the method of the invention by first sorting, from a population of cells, cells that are $\beta_2m^-$ from cells that are $\beta_2m^+$. One then selects from the $\beta_2m^-$ cells the stem cell of interest; this is performed by sorting cells by their expression of a known cell marker. Any marker that is known to be associated with stem cells may be used. Preferred such markers are proteins encoded by HLA (human leukocyte antigen) or MHC (major histocompatibility complex) genes. These include, for example, HLA markers such as RT1A, RT1B, RT1D, and hematopoietic stem cell markers such as Thy-1, flt-3, CD 34, c-Kit, and CD38. Thy-1 is especially preferred; the inventors have discovered that Thy-1 is specific for hepatocyte stem cells. U.S. Pat. Nos. 6,127,135; 6,090,622; and 5,643,741, the disclosures of which are hereby incorporated by reference, describe still additional stem cell markers. Any of these markers may be used to select, from the population of $\beta_2m^-$ cells, the stem cell of interest. A list of preferred markers is presented in Table 1.

TABLE 1

MARKERS USED TO IDENTIFY LIVER STEM CELLS AND NEURONAL STEM CELLS

| MARKER | SUPPLIER OF ANTIBODIES TO MARKER | SPECIES Rat/rabbit/m/g | ANTI-RAT/MOUSE/HUMAN? r/m/h | MONOCLONAL OR POLYCLONAL? m/p |
|---|---|---|---|---|
| Albumin human Albumin | Accurate Chemical & Scientific Corporation, Westbury, NY | Rabbit | Rat | P |
| Albumin mouse anti rat (special) | | m | rat | p |
| AFP | Santa Cruz Biotechnology, Santa Cruz, CA | Goat | H | P |
| CK19 | Amersham | | | M |
| CD34 | Santa Cruz Biotechnology, Santa Cruz, CA | Rabbit | H | P |
| CD34 | Santa Cruz Biotechnology, Santa Cruz, CA | Mouse | | M |
| CD38 (M-19) | Santa Cruz Biotechnology, Santa Cruz, CA | Goat | | P |
| c-Kit | Santa Cruz Biotechnology, Santa Cruz, CA | Rabbit | M,R,H | |
| c-Kit Oncoprotein | Novocastra Laboratories, Newcastle upon Tyne, UK | M | H | M |
| Thy-1 | Santa Cruz Biotechnology, Santa Cruz, CA | Goat | H | P |
| Flt-3/Flk-2 (S-18) | Santa Cruz Biotechnology, Santa Cruz, CA | Rabbit | | P |
| IL-3Ralpha | Santa Cruz Biotechnology, Santa Cruz, CA | Rabbit | M/Rat | P |
| RT1A | PharMigen, San Diego, CA | M | Rat | M |
| RT1A (FITC) | PharMigen, San Diego, CA | M | Rat | M |
| RT-1A | Harlan Sera-Lab, Belton, Loughborough, UK | M | Rat | M |
| RT1B (FITC)- | PharMigen, San Diego, CA | M | Rat | M |
| RT1D | Pharmigen, San diego, CA | M | R | M |
| RT1D | Pharmigen, San Diego, CA | M | Rat | M |
| RT1D (FITC) | Pharmigen, San Diego, CA | M | Rat | M |
| Beta-2-microglobulin | NeoMarkers, Inc. Fremont, CA | Mouse | human | monoclo |
| Beta-2-microglobulin | Santa Cruz,Biotechnology, Santa Cruz, CA | G | M | P |
| Beta-2-microglobulin | Pharmingen | M | Rat | M |
| Anti-Rat Macrophage Subset | Pharmigen, San Diego, CA | M | Rat | M |
| Desmin | Novocastra Laboratories, Newcastle upon Tyne, UK | M | H | M |
| alpha SMA | Sigma, Saint Louis, Missouri | M | H | M |
| GFAP | Sigma, Saint Louis, Missouri | Rabbit | | |
| Vimentin | Santa Cruz Biotechnology, Santa Cruz, CA | Goat | H | P |
| Mouse IgG1, Normal Rabbit Serum (Blocking Grade) | Pharmingen International Rockland, Gilbertsville, PA | Mouse Rabbit | h | M |
| Anti-Goat-FITC | Santa Cruz Biotechnology, Santa Cruz, CA | Donkey | goat | P |
| Mouse-anti Human HLA-B27 | Serotec Ltd, Kiddington, Oxford, GB | M | H | |
| Mouse Anti Human HLA-B7:RPE | Serotec Ltd, Kiddington, Oxford, GB | M | H | |
| Mouse Anti Human HLA-ABC | Serotec Ltd, Kiddington, Oxford, GB | M | H | |
| Rat Anti Human HLA Class I | Serotec Ltd, Kiddington, Oxford, GB | Rat | H | |
| HLA-A AB-1 | Neo Markers, Union City, CA | M | H | M |
| HLA-DP Ab-1 | Neo Markers, Union City, CA | M | H | M |
| Mouse (Monoclonal) anti-Human HLA Class | Biiosource International, Camarillo, CA | M | H | M |

TABLE 1-continued

MARKERS USED TO IDENTIFY LIVER STEM CELLS AND NEURONAL STEM CELLS

| MARKER | SUPPLIER OF ANTIBODIES TO MARKER | SPECIES Rat/rabbit/m/g | ANTI-RAT/MOUSE/HUMAN? r/m/h | MONOCLONAL OR POLYCLONAL? m/p |
|---|---|---|---|---|
| I Unconjugated Mouse MHC Class II(1-A) | Accurate Chemical & Scientific Corporation, Westbury, CA | M | Rat | |
| Rat Anti Human HLA-DR/Mouse H-2 I-A | Serotec Ltd, Kiddington, Oxford, GB | rat | H | |
| Mouse anti Human HLA DQ Class II | Serotec Ltd, Kiddington, Oxford, GB | M | H | |
| Mouse Anti Human MHC class II (DP) antigen | Serotec Ltd, Kiddington, Oxford, GB | M | H | |
| Mouse Anti Human HLA, DR, DP, DQ | Serotec Ltd, Kiddington, Oxford, GB | M | H | |
| R-PHYCOERYTHRIN Anti-Rabbit IgG (H + L) *affinity purified | Vector, Burlingame, CA | Goat | Rabbit | |
| FITC-Conjugated F(ab')2 Fragment of Rabbit Anti-Mouse IgG | Dako, Glostru, Denmark | Rabbit | M | |
| R-PHYCOERYTHRIN Anti-Mouse IgG (H + L) *affinity purified | Vector, Burlingame, CA | Horse | M | |
| FITC-Conjugated Mouse Anti Human Momoclonal antibody | PharMigen | M | H | M |
| FITC-Conjugated Mouse Anti Human Momoclonal antibody | PharMigen | M | H | M |
| PHYCOPROBE RE Anti Goat IgG (H + L) | Biomeda, Foster City, CA | Rabbit | G | |
| AMCA-conjugated Affini Pure Goat Anti-Mouse IgC | Accurate Chemical & Scientific Corporation, Westbury, NY | G | M | |
| HLA Class 1 Antigen-A2 (IgG) | US Biological, Swampscott, Massachusetts | M | H | |
| Rfx-b | Santa Cruz Biotechnology, Santa Cruz, CA | G | H | P |
| CREB-1 | Santa Cruz Biotechnology, Santa Cruz, CA | Rabbit | H | P |
| XBP-1 | Santa Cruz Biotechnology, Santa Cruz, CA | M | M | M |
| CIR | Santa Cruz Biotechnology, Santa Cruz, CA | G | H | P |
| HLA-B Ab-1 | Neomarkers, Union City, CA | M | H | M |
| B&-1 | Santa Cruz Biotechnology, Santa Cruz, CA | Rabbit | H | P |
| B7-2 | Santa Cruz Biotechnology, Santa Cruz, CA | Rabbit | H | P |
| RBP-J kappa | Santa Cruz Biotechnology, Santa Cruz, CA | G | H | P |
| R-PHYCOERYTHRIN (R_PE)-Conjugated Mouse Anti-Human | Pharmigen, San Diego, CA | M | H | M |

TABLE 1-continued

MARKERS USED TO IDENTIFY LIVER STEM CELLS AND NEURONAL STEM CELLS

| MARKER | SUPPLIER OF ANTIBODIES TO MARKER | SPECIES Rat/rabbit/m/g | ANTI-RAT/MOUSE/HUMAN? r/m/h | MONOCLONAL OR POLYCLONAL? m/p |
|---|---|---|---|---|
| Monoclonal Antibody NF Kappa p65 | Santa Cruz Biotechnology, Santa Cruz, CA | R | H | P |
| Mouse (Monoclonal) anti-Human HLA Class I DR (monomorphic) Purified | Biosource International, Camarillo, Ca | M | H | M |
| Monoclonal Mouse Anti-Human Class I Antigen | Dako, Glostrup, Denmark | M | H | M |
| ISGF-3 gamma p48 | Santa Cruz Biotechnology, Santa Cruz, CA | Rabbit | H | P |
| HLA-A AB-1 | NeoMarkers, Inc. Union city,CA | Mouse | H | M |
| Anti human HLA Class I unconjugated | Biointernational Camarillo,CA | Mouse | H | M |
| HIA-A-Ab1 | NeoMarkers fremont,CA | Mouse | H | M |
| HIa-DR-AB-1 | Neo markers Fremont CA | Mouse | H | M |
| Mouse (monoclonal) Anti-human Fas Ligand (FasL) Unconjugated | | M | H | M |
| Anti Neurokinin3 | NOVUS bilogicals | Rabbit | R | P |
| TAP 1 | Rockland gilbertsville PA | Rabbit | H | P |
| IgG2b | Transduction Labratories, lexington, KY | Mouse | H | |
| IgG3 | Chemicon Intl., Temecula, CA | Mouse | H | M |
| IgG1, | PharMingen Intl. | Mouse | H | M |
| HLA-DR | Cedarlane, Hornby, Ontario, Canada | Rat | H | |
| Alpha-actin | Cedarlane, Hornby, Ontario, Canada | M | | |
| Rabbit anti-Calreticulin | RDI, Flanders, NJ | Rabbit | H/Rabbit/M/Rat | |
| Mouse-anti-Calnexin Monoclonal ab | RDI, Flanders, NJ | M | H/rat/M | M |
| Goat anti GRP | RDI, NJ | Goat | H | P |
| HSP70 AB-2 | NeoMarkers, Fremont, Ca | Mouse | H/M/R | M |
| Rt1 MHC-II | Accurate Chemical &Scientific Corporation, | Mouse | | |
| Anti-Serotonin | Cappel, Aurora, Ohio | Rabbit | H/M/r | p |

Any population of cells where stem cells are suspected of being found may be sorted according to the method of the invention. Preferably, cells are obtained from the bone marrow of a non-fetal animal, and most preferably from a human. Fetal cells may also be used; the method of the invention may be used, for example, to obtain from such cells fetal neuronal stem cells. U.S. Pat. Nos. 6,204,053 B1 and 5,824,489, the disclosures of which are hereby incorporated by reference, identify additional sources of cells that contain or are thought to contain stem cells; any of these cells may be sorted according to the method of the invention.

Cell sorting may be by any method known in the art to sort cells. A preferred sorting procedure is by fluorescent activated cell sorting (FACS). Magnetic bead cell sorting (MACS), and an improvement to it the inventors have developed—double magnetic bead cell sorting (D/MACS)—are especially preferred. The conventional MACS procedure is described by Miltenyi et al., "High Gradient Magnetic Cell Separation with MACS," *Cytometry* 11:231–238 (1990). To sort cells by MACS, one labels cells with magnetic beads and passes the cells through a paramagnetic separation column. The separation column is placed in a strong permanent magnet, thereby creating a magnetic field within the column. Cells that are magnetically labeled are trapped in the column; cells that are not pass through. One then elutes the trapped cells from the column.

In the inventor's D/MACS procedure, one labels a sample of cells with magnetic beads having antibodies to $\beta_2m^+$. In the first sorting step, one depletes $\beta_2m^+$ cells from the sample by passing the sample through an LD (milliliters) column. In the second sorting step, one positively selects cells having the marker of interest (e.g., an HLA/MHC gene-product marker, such as Thy-1) by passing the sample through an LS column. One may use the same buffer as is used in the conventional MACS procedure, except that a 0.01% solution of sodium azide is added to prevent capping of surface antigen-antibody complexes. At the end of the procedure all sorted cells are washed with mild isotonic salt solution once and then with serum free PBS three times to prevent nonspecific albumin staining.

In a presently preferred embodiment, the method of the invention is used to identify hepatocyte (Examples I and II) and neuronal (Example III) stem cells. Facultative progenitor cells such as oval cells exist in the liver and can be induced to proliferate following hepatic injury when proliferation of mature hepatocytes is suppressed with carcinogens. R. P. Evarts et al., Cancer Res. 49, 1541-7 (1989). However, the nature, origin and role of oval cells and other liver progenitors in liver development and repair remain unclear. For many years, oval cells and other liver progenitors were thought to originate from cells present in the canals of Herring or from blast-like cells located near the bile ducts. J. W. Grisham and S. S. Thorgeirsson, "Stem Cells," from C. S. Potten, Ed., Stem Cells, Academic Press, San Diego (1997); P. M. Novikoff and A. Yam, Am J Pathol 148, 1473-92 (1996).

Recently, results of cross-sex and cross-strain bone marrow and whole liver transplantation experiments performed by Petersen et al. indicated that the bone marrow may be a source of hepatocyte progenitors and can give rise to cells expressing mature hepatocyte markers (e.g., albumin, CK18, and CAM5.2). B. E. Petersen et al., Science, 284, 1168-70 (1999); M. R. Alison et al., Nature 406, 257 (2000); and N. D. Theise et al, Hepatology 32, 11-6 (2000). Further evidence for the existence of bone marrow-derived hepatocyte stem cells ("BDHSC") comes from a recent study by Lagasse et al. with fumarylacetoacetate hydrolase ("FAH") deficient mice. E. Lagasse et al., Nat Med 6, 1229-34 (2000). FAH is essential to metabolize phenylalanine; without FAH, toxic phenylalanine metabolites build up in the liver, destroying it. Lagasse et al showed that transplanting adult bone marrow cells (which contain hematopoietic stem cells) into mice that lack FAH restored their liver biochemical functions.

Previous attempts at isolating hepatocyte progenitors both from bone marrow and liver have yielded a mixture of hematopoietic and liver progenitor cells with no means of distinguishing between the two. This is because these cells all share common cell-surface receptors and antigens, including CD34, Thy-1, c-Kit, flt-3 and all known oval cell antigens. E. Lagasse et al, Nat Med 6, 1229-34 (2000); B. E. Petersen et al, Hepatology 27, 433-45 (1998); M. Omori et al, Am J Pathol 150, 1179-87 (1997); K. Fujio et al, Lab Invest 70, 511-6 (1994); and S. Brill et al, Proc Soc Exp Biol Med 204, 261-9 (1993). To date, no one has isolated explicitly and specifically committed hepatocyte progenitors from bone marrow.

Stem cells, like oval cells, are thought to be ideal targets for malignant transformation, and alterations in MHC/HLA and $\beta_2$m expression are manifested in many types of cancer cells, as well as in diseased livers where regeneration and dedifferentiation are found. See, for example, H. Kubota et al, Proc Natl Acad Sci USA 97, 12132-7 (2000) and K. N. Lowes et al., Am J Pathol 154, 537-41 (1999).

The methods described in Examples I and II are the first methods ever reported to characterize and specifically isolate BDHSC cells. The inventors have discovered—using the method of the invention described earlier—that such cells have a novel combination of common surface antigens, $\beta_2$m$^-$/Thy-1$^+$ that link blast-like cells in the bone marrow and in regenerating and malignant livers. These examples demonstrate the relative ease with which the method of the invention may be employed to isolate and propagate in culture these autologous hepatocyte stem cells. It further demonstrates the capability of BDHSC to differentiate, and re-establish, epithelial lineages following proliferation in culture, into hepatocytes and/or biliary epithelial cells. This opens new horizons in the study of liver stem cells and provides the means for direct study of BDHSC. The present invention further allows one to isolate and use these cells in an autologuous manner; this could obviate the need for immunosuppression, thereby increasing the therapeutic benefits of the present invention to patients with liver failure.

EXAMPLES

All references cited herein are hereby incorporated by reference in their entirety. The following examples are typical of the procedures that may be used to isolate stem cells according to the method of the invention. Modifications of these examples will be apparent to those skilled in the art who seek to identify different stem cells than the ones discussed here.

Example I

Isolation of Hepatocytes from Human and Rat Liver

The inventors examined a variety of tissues for the expression of MHC (HLA, RT1A, RT1B, RT1D), hematopoietic stem cell markers (Thy-1, flt-3, CD 34, c-Kit and CD38), and liver associated markers (ALB, AFP, CK8, 18, 19, and C/EBPα) using specific antibodies for immunohistochemical (IHC) staining of sections from paraffin embedded tissue and isolated cells in suspension after cytocentrifugation. Immunohistochemistry and immunofluorescence were performed utilizing the ABC method, VECTOR laboratories. Tissue specimens were fixed and placed in paraffin blocks and whole cell isolates in suspension were cyto-spun onto slides. All specimens were fixed in glyoxal. Interpretation of immunofluorescence was done using three-dimensional confocal microscopy.

Human tissue specimens (from three different individuals, 18 different specimens overall) were obtained from surgical or diagnostic biopsies. These included 1) surgical specimens of hepatocellular carcinomas; 2) specimens from patients with liver diseases known to be associated with hepatic regenerative response, such as a) primary sclerosing cholangitis; b) primary biliary cirrhosis; c) alcoholic hepatitis, and fulminant hepatic failure; 3) fetal livers from abortion products; and 4) malignant cell lines HepG2 and Hep3B. N. Fausto et al., Proc Soc Exp Biol Med, 204, 237-41 (1993) and V. J. Desmet, Prog Liver Dis 10, 89–121 (1992) describe these and related specimens.

Rat specimens included livers obtained from 21 Sprague-Dawley rats that underwent common bile duct ligation to induce liver injury resulting in a regenerative response (see N. Fausto et al., Proc Soc Exp Biol Med 204, 237-41 (1993) and "small hepatocytes" from cultures established from nonparenchymal cell fraction of adult rat livers i.e., cells, which are widely recognized as committed hepatocyte progenitors (as described by T. Mitaka et al, Biochem Biophys Res Commun 214, 3 10-7 (1995). Whole cell isolation was performed on normal (n=9) and bile duct ligated (n=21) adult male Sprague-Dawley rats. Cell harvesting was performed on day 10, after initial common bile duct ligation, by the standard two-step collagenase perfusion method. The final cell suspension was further processed using percoll density gradient, consistently achieving final viability of >95%.

Rat specimens also included livers from twelve newborn pups. A two-step non-perfusion, liver cell isolation from newborn rats (1, 4 and 24 days) was performed. Livers were removed three at a time, dissected and placed in 0.9% saline to remove blood, then minced and shaken in a water bath at 38° C. in EDTA. The supernatant was discarded and the liver tissue was suspended in Leffert's buffer with 0.05% calcium enriched collagenase IV. This procedure was followed by three 10 mm incubations at 38° C. in a shaking water bath. At the end of each digestion, the supernatant was collected and fresh collagenase solution was added. The dispersed cells were resuspended in ice cold DMEM containing 10% FBS and filtered through a 100 $\mu$m mesh. The resulting cell suspension was centrifuged at 4° C. for 2 minutes, the pellet re-suspended in DMEM with 10% FBS and placed on ice. Cell variability was greater than 95% (trypan blue exclusion).

Quantitative analyses, on stained slides (IHC), were done independently by two different investigators. Each stain was repeated three times on the various specimens and 20 random fields were examined. All numbers were computed using Jandel Scientific 1.0 software. When indicated, the liver cell mass was estimated to be composed of 4% of body weight, e.g., $7 \times 10^8$ hepatocytes for a 250 g rat.

Figure 1:
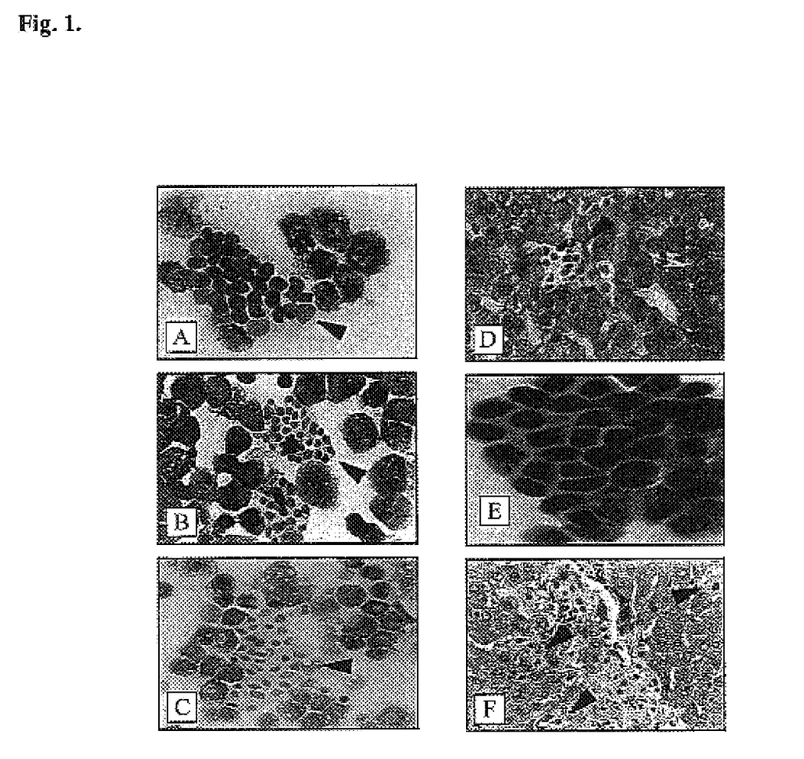
FIG. 1 shows immunohistochemistry staining for $\beta_2$microglubulin ($\beta_2$m) of paraffin liver sections and cytospun cells from whole liver cell preparations. The solid arrow identifies bone-marrow-derived hepatocyte stem cells.

A significant finding in all source material was the presence of small (5–8 $\mu$m diameter) blast-like cells with small nuclei and scant cytoplasm (high nuclear to cytoplasmic ratio) containing only a few organelles (FIG. 1). These cells—in contrast to all other nucleated cells—did not express $\beta_2$m. In normal rat livers these cells were occasionally seen near the portal tracts and amounted to less than 0.01±0.001% of the rat liver cell mass. In contrast, in diseased rat livers they were numerous (4.5±1.5%), frequently in small clusters and apparently "streaming" from zone-1 into zone-2. They were never observed in zone-3 of the hepatic acini.

During this "migration," cells differentiated morphologically into mature hepatocytes, exhibited increase in cytoplasmic granularity, lost their expression of AFP, and maintained expression of ALB (FIG. 1E). To identify the hematopoietic stem cell markers these $\beta_2$m⁻ cells expressed, rat livers obtained from common bile duct ligation were separated into $\beta_2$m⁺ and $\beta_2$m⁻ populations using MACS. Hematapoietic stem cell markers—Thy-1, flt-3, CD 34, c-Kit and CD38—were identified by immunohistochemical analysis. Among these, Thy-1 was expressed in 99±2.0% of the $\beta_2$m⁻ fraction obtained from whole cell preparation of common bile duct ligation rat livers (FIG. 1F). Moreover, using the $\beta_2$m⁻/Thy-1⁺ fraction from whole cell preparations of common bile duct rat livers and a triple immunohistochemical staining technique, the inventors found that these cells (the $\beta_2$m⁻/Thy-1⁺ cells) also expressed AFP, ALB and CK8, but not CK18 or CK19. These findings suggest that bone marrow-derived hepatocyte stem cells are potentially in an earlier developmental stage than hepatic blasts or oval cells. See S. S. Thorgeirsson, *Faseb J* 10, 1249-56 (1996), for a description of hepatic blasts and oval cells. These data show that $\beta_2$m⁻/Thy-1⁺ cells are committed hepatocyte progenitors.

Example II

Isolation of Hepatocyte Stem Cells from Bone Marrow

Using the D/MACS procedure described earlier, $\beta_2$m⁻ cells were isolated from the bone marrow of three common bile duct ligation rats. From this population of cells, the inventors selected five different subpopulations: CD34⁺, c-Kit⁺, flt-3⁺, Thy-1 and Thy-1⁺. The inventors then stained the various sorted cells for ALB. Among these five subpopulations, only the Thy-I⁺ had a nearly complete positive albumin signal (99.9±1.2%). In comparison to the c-Kit⁺ that had 5–10% and in contradistinction to the Thy-1⁻ cells that did not expressed albumin. Based on these results, the inventors postulated that $\beta_2$m⁻/Thy-1⁺ fraction of the total bone marrow represents bone marrow derived hepatocyte stem cells.

Figure 2:
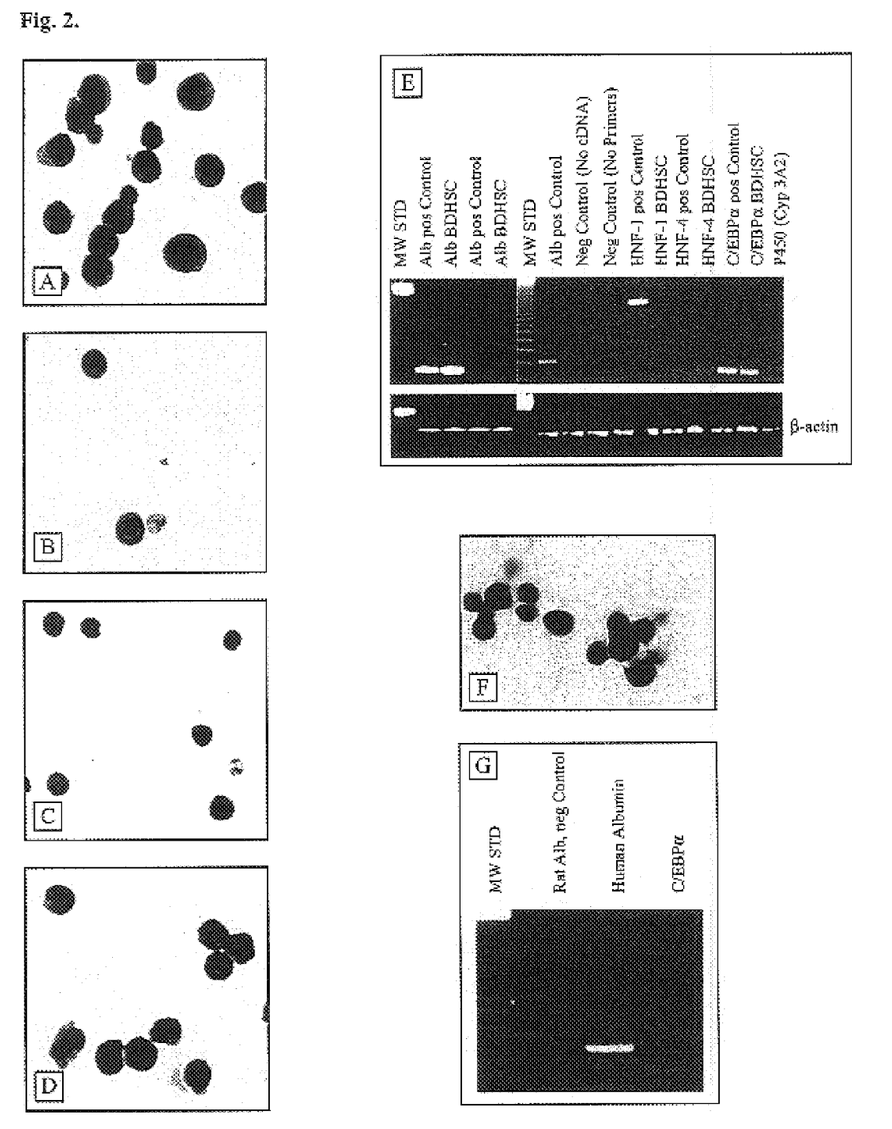
FIG. 2 shows the result of RT-PCR and immunohistochemistry studies on $\beta_2m^-$/Thy-1$^+$ cells (bone marrow-derived hepatocyte stem cells) purified from bone marrow (human and rat), utilizing a two-step magnetic bead cell sorting procedure (D/MACS).

Nine additional Sprague-Dawley rats underwent common bile duct ligation and the bone marrow was harvested after 10 days. The $\beta_2$m⁻/Thy-1⁺ fraction was obtained and cells were cyto-spun onto slides and stained for ALB, AFP, CK8, CK18, CK19 and C/EBPα. Additional cells were sorted directly into cell lysis-buffer and one step single cell RT-PCR was performed. All RT-PCR procedures were performed using hot start, single cell, one step technology on equipment from QIAGEN. At the protein level, these $\beta_2$m Thy-1⁺ bone marrow derived hepatocyte stem cells express ALB, AFP, CK8 and C/EBPα (98.9±1%, 75±10.0% 95±3.0% and 99±0.5% respectively) (FIGS. 2A–D) and at the mRNA level, these cells express ALB, C/EBPα, p450 (Cyp3A2), HNF-4 but not HNF-1 (FIG. 2E). Quantitatively, the $\beta_2$m⁻ fraction obtained from normal bone marrow (n=7), represented 0.45%±0.60% of the total cell mass in the bone marrow while the same fraction obtained from the bone marrow of common bile duct ligation rats (n=7) represented 3.66±0.1%. Of these fractions, bone marrow derived hepatocyte stem cells ($\beta_2$m⁻/Thy-I⁺) represented 1.9±1.6% and 5.5±2.3%, or $8.5 \times 10^{-5}$ and $2.0 \times 10^{-3}$ of the total nonerythroid bone marrow cell mass respectively.

Utilizing the same magnetic bead cell sorting procedure, the $\beta_2$m⁻/Thy-1⁺ fraction was extracted from six normal human bone marrow samples. All of the samples studied expressed ALB and its transcription factor C/EBPα both at the mRNA and protein levels (FIGS. 2F–H). To assure the accuracy of these studies, four different $\beta_2$m, three albumin, and two Thy-1 antibodies were used. In addition, the inventors used two different sets of albumin primers, including nested primers to increase the sensitivity and specificity of the findings.

Freshly isolated BDHSC can be characterized as hepatocyte progenitors as assessed by expression of ALB, AFP, CK8, C/EBPα and HNF-4. After culturing these cells clearly differentiated into mature hepatocytes, which exhibited ureagenesis from ammonia and expressed ALB, C/EBPα, CAM5.2 and additionally by de-novo expression of HNF-I. These effects are enhanced several fold after co-culture with autologus hepatocytes and serum obtained from rats with cholestasis.

To establish the hepatic nature of the bone marrow derived hepatocyte stem cells, the inventors examined their functional characteristics in vitro. A culture system was designed to simulate the cholestatic regenerative response/ signal in vivo. (FIG. 3A) This culture system was constructed of two chambers, separated by a semi-permeable membrane (pore size 0.4 $\mu$m). The top chamber was coated with collagen type-I and contained hepatocytes isolated from common bile duct ligation rat livers. The bottom chamber was coated with laminin containing "MATRIGELO," collagen type-IV, TNF-β and aFGF, and contained the corresponding autologous BDHSC isolated from bone marrow extracted from six different femurs. The modified media contained 5% autologous "toxic" serum. This serum is obtained from autologous common bile duct ligation rats and is thought to contain humoral factors that have a role in signaling the BDHSC to proliferate, differentiate, and migrate to the injured liver. Dexamethasone and IL3 were added to the media after 72 hours to enhance differentiation and proliferation. BDHSC were co-cultured with autologous hepatocytes using the Costar Transwell COL inlay (Corning Costar Corporation). The inlay was seeded with 50,000 hepatocytes/cm$^2$ and the Matrigel coated (25 μg/cm$^2$) lower compartment contained the BDHSC. HGF (25 ng/ml) and autologous serum (5%) was added to the regular small hepatocyte culture media as described by Mitaka et al, *Biochem Biophys Res Commun* 214, 3 10-7 (1995).

Figure 3:
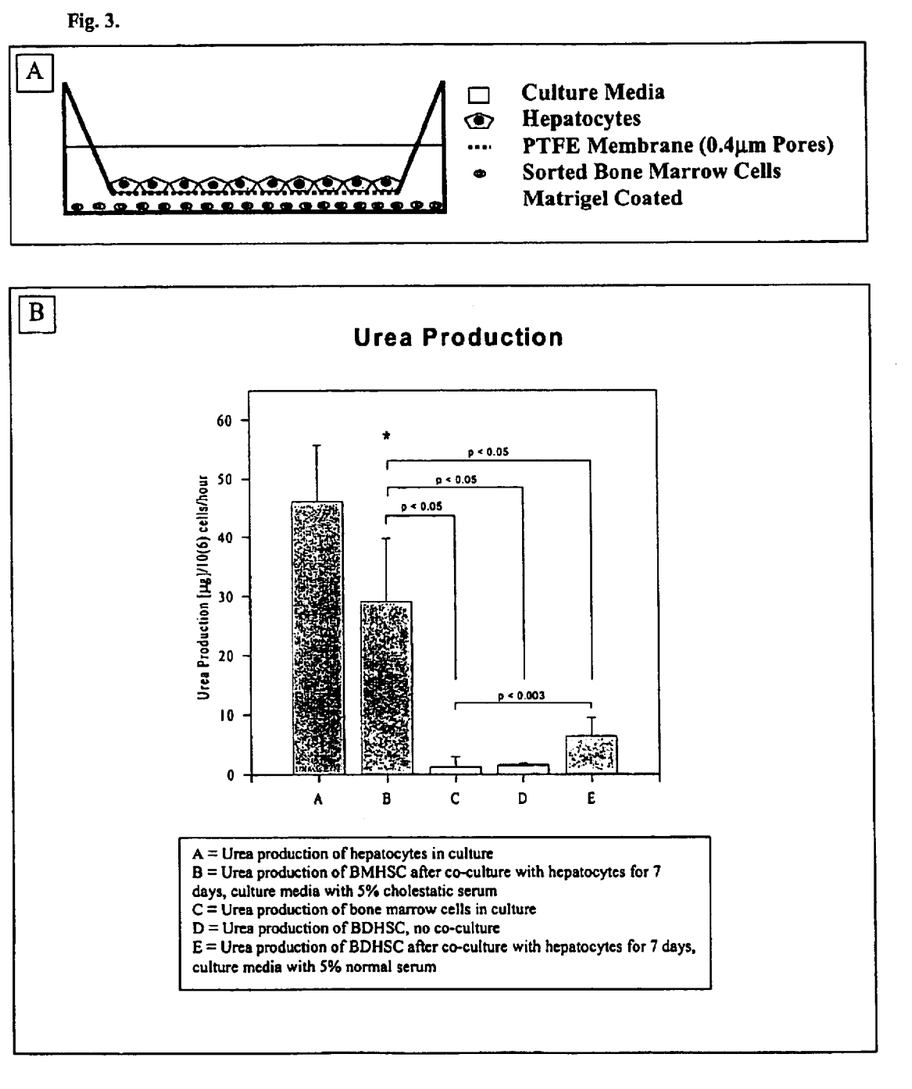
FIG. 3 illustrates a cell culture system simulating liver regenerative response environment.

The chambers were separated and placed in fresh serum free media at days 3, 5 and 7. Each of the twelve cell colonies was than challenged with 1.5 mM ammonia for 8 hours. Ammonia clearance and ureagenesis were measured using a calorimetric assay. Ammonia clearance and ureagenesis was determined by an enzymatic colorimetric test (Boehringer-Mannheim). Results were analyzed by ANOVA and Fisher's exact test (Jandel Statistical Software, version 1.0) and found to be statistically significant. The results are shown in FIG. 3B.

The functional study described in this example showed that the BDHSC, after co-culture with injured hepatocytes isolated from cholestatic livers and autologous "toxic" serum, could metabolize ammonia into urea, a highly specific hepatocyte function. This function is described in S. G. Powers-Lee and A. Meister, "Urea Synthesis and Ammonia Methabolism," in I. M. Arias et al., Eds., *The Liver: Biology and Pathobiology* (Raven Press, Ltd. New York, ed. second edition, 1988).

Some reports describe ureagenesis by macrophages. Macrophages, however, need L-arginine as a substrate, a substance that was excluded from the culture media of this example. A negative signal after staining with monoclonal antibody specific for rat macrophages further suggests that the inventor's cells are not macrophages. Data from 18 different experiments performed on BDHSC and hepatocytes purified from bone marrow obtained from six different femurs showed that BDHSC produced 29 μg of urea per 10$^6$ cells/hour in comparison to 46 μg of urea produced by their autologous hepatocytes. These results were compared to data obtained from controls consisting of normal whole bone marrow extracted from three different animals and cultured in the same manner. Strikingly, the control bone marrow did not metabolize ammonia into urea (p<0.05). Further controls from three additional animals were performed using BDHSC alone from normal animals and BDHSC that were co-cultured with non-cholestatic autologous hepatocytes (FIG. 3B). Results from these experiments demonstrated that BDHSC alone did not differentiate efficiently into ammonia metabolizing cells although they exhibited a small degree of ureagenesis. In contradistinction, the same cells (BDHSC) co-cultured with autologous hepatocytes isolated from normal animals did express de-novo ureagenesis (P<0.003) (FIG. 3B). This suggests that BDHSC require as yet undefined humoral factor(s), possibly contained in cholestatic sera to fully differentiate into functioning hepatocytes (p<0.05).

Further characterization of these BDHSC was performed on day 7. Double immunofluorescence studies revealed that in these cultures BDHSC express both the hepatocytic marker CAM5.2 (as described by T. S. Lai Y S et al, *Arch Pathol Lab Med*, 113, 134–138 (1989)) and albumin, as well. Three-dimensional confocal-microscopy showed co-localization of both ALB and CAM5.2 signals to the cytoplasm of BDHSC (FIGS. 4A–B). To further confirm expression of ALB, ALB gene expression was examined at the mRNA level utilizing single cell one step RT-PCR. The results confirmed expression of ALB, its transcription factor C/EBPα and de-novo expression of HNF-1. Interestingly, these cells lost the expression of HNF-4 after culturing (FIG. 4C).

Figure 4:
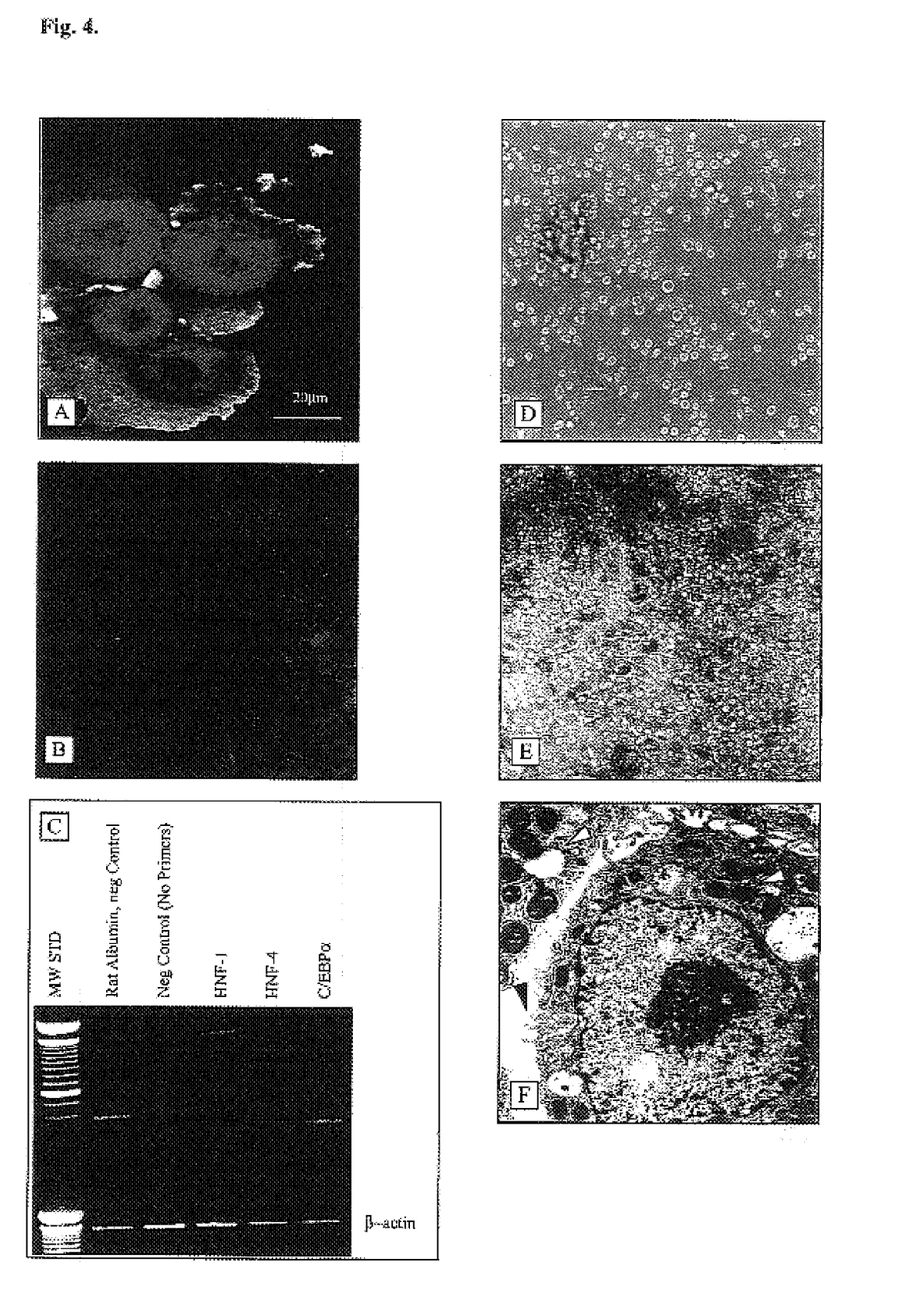
FIG. 4 illustrates the characterization of bone marrow-derived hepatocyte stem cells in culture.

After 7 days in culture, each dish contained several aggregates of cells, which morphologically resembled hepatocytes (FIGS. 4D–E). Transmission electron microscopy was used to examine the ultra structure of these cells. The resulting micrographs demonstrated hepatocyte morphology (FIG. 4F). While some BDHSC transformed into committed hepatocytes morphologically, the remaining cells did not change morphology but underwent extensive proliferation. Cultures were initially plated with 5×10$^4$ cells per dish. On day 7, expansion to 1.5–2.0×10$^6$ cells/dish occurred representing five to six cell divisions, or about one cell cycle per 24 hours. Of note, in control dishes of BDHSC that were co-cultured with autologous hepatocytes obtained from normal animals, similar cellular aggregates and proliferative responses were not observed but the cells did metabolize ammonia into urea although, to a much lesser degree.

The observations made in this example demonstrate that the adult (human and rat) bone marrow contains a sub-population of cells with stem-cell-like properties and that these cells can function as hepatocytes with appropriate stimuli. The necessity of the interaction between injured hepatocytes and BDHSC, likely via a humoral factor, was demonstrated by the lack of liver specific function (ammonia metabolism and ureagenesis) when BDHSC were grown in non-toxic serum and without injured hepatocytes (FIG. 3B). This finding is similar to what is seen during embryogenesis, where interaction of committed endodermal cells with mesenchymal components of the primitive liver appears to be critical for proper lineage development and differentiation. It then follows that the epithelial stem-cell-like hepatocyte progenitor cells of the adult bone marrow may phenotypically resemble hepatoblasts of the fetal liver as demonstrated in our study. Additionally, the compartment-type zonation of sublobular ureagenesis gene expression, which was described by Haussinger lead further credence to our findings; the higher concentration of these BDHSC in the periportal area and their ability to produce urea from ammonia.

The evidence presented suggests that these BDHSC are at an earlier developmental stage than oval cells or hepatoblasts. Therefore, these cells might possess earlier or greater pluripotential capabilities. Early liver development coincides with the expression of a subset of hepatocyte-enriched-transcription-factors (HETF) like HNF-4 and HNF-1. F. M. Sladek, *Receptor* 4, 64 (1994); M. Ott et al., *Gene Expr* 8, 175-86 (1999). HETF are expressed prior to the emergence of cells recognized to be committed liver lineages and expression of these genes is crucial in the determination and characterization of early liver cells, in particular the CCMT/enhancer binding protein C/EBPα. Hepatoblasts that express ALB, AFP, HNF-4 and HNF-I represent the earliest committed liver cells in the developing embryo. BDHSC do not express HNF-I early on. However, following culture with a putative humoral factor(s) (possibly contained in "toxic" serum from cholestatic rats), these cells clearly differentiate into hepatocytes and some possibly into cholangiocytes acquiring expression of HNF-1 and CK19 while losing expression of AFP. This example demonstrated significant proliferative activity in vitro as well as manifestation of morphological characteristics and expression of liver specific differentiated functions in these BDHSC.

Example III

Isolation of Neural Stem Cells

Neural progenitors were harvested from the mesencephalic, striatal, and cortical regions of 24 week old human abortus fetal brain. The tissue was dissected into 0.5 cm pieces using a scalpel in sterile phosphate buffered saline (PBS, ph 7.4, Life Technologies). It was then transferred into a 50 ml Falcon tube containing 15 ml of 0.25% Trypsin solution in Versene (Life Technologies). The tissue was incubated for 10 minutes at 37° C. and subsequently 15 ml of trypsin neutralization solution (Clonetics) was added. The tissue was then mechanically dissociated using a glass pipette and centrifuged a 1000 rpm. The supernatant was aspirated and discarded.

The pellet containing dissociated cells was resuspended in B27 growth medium (Dulbecco's Modified Eagle Medium with additional nutrient mixture F12-Ham 1:1, Life Technologies) to which 2 μg/ml of Heparin (Sigma, St. Louis) and penicillin-streptomycin solution (100μ/ml and 100 μg/ml respectively, Life Technologies) was added. The dissociated cells were plated at a density of approximately 100,000 cells/ml and were grown on uncoated T75 (Falcon, USA) plastic flasks in B27 medium with additional human bFGF and LIF (20 ng/ml each, PeproTech). The cells grew as free-floating clusters ("neurospheres") and were prevented from attachment by gently tapping the flasks each day. The neurospheres were mechanically dissociated every 7 days and when a density of $5 \times 10^5$ cells/ml was achieved, cells were propagated to a new flask.

Approximately 100,000 cells were taken as neurospheres to be sorted by FACS (Dickinson, USA). The neurospheres were incubated in PBS with 0.25 mM EDTA for 5 minutes, then were transferred into a B27 medium. Thereafter, the neurospheres were further dissociated (mechanically) into single cells. The cells were then centrifuged for 5 minutes at 300 g. The supernatant was discarded, and the cells were resuspended in DMEM/F12 or PBS to achieve a concentration of $1 \times 10^8$ cells/ml. Primary antibodies were added at 10 μl per 50 μl of cell suspension and incubated for 30 minutes at 40° C. Antibodies to $\beta_2$m were added in a 1:175 ratio (1 part $\beta_2$m to every 175 parts cell suspension) and antibodies to HLA class II were added in a 1:200 ratio. 10 times volume of DMEM/F12 or PBS was added and the cells were washed for 5 minutes. Cells were centrifuged for 5 minutes at 300 g and the supernatant was discarded.

Secondary FITC-conjugated antibodies (1:50) were added at 50 pi per 50 μl of cell suspension. Cells were incubated for 30 minutes at 4° C. 10 times volume of DMEM/F12 or PBS was added and the cells were washed for 5 minutes. Cells were centrifuged for 5 minutes at 300 g and the supernatant was discarded. Cells were resuspended in 400 μl of DMEM and were transferred to a FACS machine.

Cells sorted by FACS were differentiated by plating them on glass slides coated with laminin (40 mg/ml, Boehringer Mannheim). All-trans retinoic acid (10-6 M, Sigma), dibutyryl cyclic AMP (1 mM, Sigma) and brain-derived neurotrophic factor (20 ng/ml, Peprotech) were added to the growth media. The cells were differentiated for 5 and 10 days and then stained for specific neuronal markers ($\beta$-III tubulin and MAP2 a&b).

Class I and $\beta_2$m expression were found to be low and heterogenous on the cell surface of neuronal progenitor cells. Post differentiation, class I expression decreased significantly and $\beta_2$m expression became high and homogenous in more differentiated cells. Undifferentiated progenitors did not express TAP or class II while differentiation stimulated expression of both. CLIP and class II/DM expression increased significantly after stimulation. The foregoing demonstrates that the expression of class I and II products of HLA varies widely in a predictable and specific manner among heterogeneous neuronal progenitors, thereby permitting one to sort between true neuronal and other progenitor cells (e.g., oligodendroglia, astrocytes, etc.) according to their pattern of HLA expression.

Those skilled in the art will recognize, or be able to determine using no more than routine experimentation, variations on the foregoing examples that will permit them to identify many other stem cells than the ones described herein.

What is claimed is:

1. A method for the isolation of stem cells of a mammal, the method comprising:

obtaining a sample of cells from the mammal;

sorting, from the sample, cells that express $\beta_2$-microglobulin from cells that do not express $\beta_2$-microglobulin; and selecting by a stem cell surface marker stem cells from the sample of cells that do not express $\beta_2$-microglobulin.

2. The method of claim 1, wherein the step of sorting comprises sorting by fluorescent activated cell sorting.

3. The method of claim 1, wherein the step of sorting comprises sorting by magnetic bead cell sorting.

4. The method of claim 1, wherein the step of sorting comprises sorting by double magnetic bead cell sorting.

5. The method of claim 1, wherein the step of selecting stem cells further comprises sorting.

6. The method of claim 5, wherein the stem cell marker is a protein expressed by one or more genes encoding the major histocompatibility complex.

7. The method of claim 6, wherein the one or more genes encode human leukocyte antigens.

8. The method of claim 5, wherein the marker is Thy-1.

9. The method of claim 5, wherein the marker is selected from the group consisting of RT1A, RT1B, and RT1D.

10. The method of claim 5, wherein the marker is selected from the group consisting of flt-3, CD 34, c-Kit, and CD38.

11. The method of claim 5, wherein the step of selecting stem cells further comprises sorting by fluorescent activated cell sorting.

12. The method of claim 5, wherein the step of selecting stem cells further comprises sorting by magnetic bead cell sorting.

13. The method of claim 5, wherein the step of selecting stem cells further comprises sorting by double magnetic bead cell sorting.

14. The method of claim 1, wherein the sample of cells is obtained from an adult mammal.

15. The method of claim 1, wherein the sample of cells is obtained from a fetus.

16. The method of claim 1, wherein the sample of cells is obtained from bone marrow.

17. The method of claim 1, wherein the sample of cells is obtained from the liver of a mammal.

18. The method of claim 1, wherein the sample of cells is obtained from the brain of a mammal.

19. A method for the isolation of stem cells of a mammal, the method comprising:

obtaining a sample of cells from the mammal;

sorting, from the sample, cells that express $\beta_2$-microglobulin from cells that do not express $\beta_2$-microglobulin; and sorting, from the sample of cells that do not express $\beta_2$-microglobulin, cells that express a stem cell surface marker from cells that do not express a stem cell surface marker.

20. The method of claim 19, wherein the step of sorting comprises sorting by fluorescent activated cell sorting.

21. The method of claim 19, wherein the step of sorting comprises sorting by magnetic bead cell sorting.

22. The method of claim 19, wherein the step of sorting comprises sorting by double magnetic bead cell sorting.

23. The method of claim 19, wherein the stem cell marker is a protein expressed by one or more genes encoding the major histocompatibility complex.

24. The method of claim 23, wherein the one or more genes encode human leukocyte antigens.

25. The method of claim 19, wherein the marker is Thy-1.

26. The method of claim 19, wherein the marker is selected from the group consisting of RT1A, RT1B, and RT1D.

27. The method of claim 19, wherein the marker is selected from the group consisting of flt-3, CD 34, c-Kit, and CD38.

28. The method of claim 19, wherein the sample of cells is obtained from an adult mammal.

29. The method of claim 19, wherein the sample of cells is obtained from a fetus.

30. The method of claim 19, wherein the sample of cells is obtained from bone marrow.

31. The method of claim 19, wherein the sample of cells is obtained from the liver of a mammal.

32. The method of claim 19, wherein the sample of cells is obtained from the brain of a mammal.

33. The method of claim 19, wherein the cells that express a stem cell marker are pluripotent stem cells.

34. The method of claim 19, wherein the cells that express a stem cell marker are embryonal stem cells.

* * * * *